(12) United States Patent
Era et al.

(10) Patent No.: US 8,119,613 B2
(45) Date of Patent: Feb. 21, 2012

(54) THERAPEUTIC AGENT FOR NEUROBLASTOMA TARGETING ARID3B

(75) Inventors: Takumi Era, Hyogo (JP); Shin-Ichi Nishikawa, Hyogo (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 12/858,892

(22) Filed: Aug. 18, 2010

(65) Prior Publication Data
US 2011/0039912 A1 Feb. 17, 2011

Related U.S. Application Data

(62) Division of application No. 12/087,017, filed as application No. PCT/JP2006/325467 on Dec. 21, 2006, now abandoned.

(30) Foreign Application Priority Data

Dec. 26, 2005 (JP) .................................. 2005-372530

(51) Int. Cl.
*C12N 15/11* (2006.01)
*C12Q 1/68* (2006.01)
*G01N 33/53* (2006.01)

(52) U.S. Cl. .......................... 514/44 A; 435/7.1; 435/6.1
(58) Field of Classification Search ................... 435/6.1, 435/7.1; 514/44 A
See application file for complete search history.

(56) References Cited

FOREIGN PATENT DOCUMENTS

| JP | 2005-160354 A | 6/2005 |
|---|---|---|
| JP | 2005-304497 A | 11/2005 |
| WO | WO 2004/096826 A2 | 11/2004 |

OTHER PUBLICATIONS

Brodeur, G.M., "Neuroblastoma: Biological Insights Into a Clinical Enigma," *Nat. Rev. Cancer 3*:203-216, Nature Publishing Group (Mar. 2003).
Kobayashi, K., et al, "ARID3B Induces Malignant Transformation of Mouse Embryonic Fibroblasts and Is Strongly Associated with Malignant Neuroblastoma," *Cancer Res. 66*:8331-8336, American Association for Cancer Research (Sep. 2006).
Nishikawa, S., "A Database of Functional Genomics Related to Embryonic Stem (ES) Cells," *Japanese Scientific Monthly 59*:227-230, Japan Society for the Promotion of Science (Apr. 2006).
Unverified English Language Translation of Nishikawa, S., "A Database of Functional Genomics Related to Embryonic Stem (ES) Cells," *Japanese Scientific Monthly 59*:227-230, Japan Society for the Promotion of Science (Apr. 2006).
Numata, S., et al., "Bdp, a New Member of a Family of DNA-binding Proteins, Associates with the Retinoblastoma Gene Product," *Cancer Res. 59*:3741-3747, American Association for Cancer Research (1999).
Strieder, V., and Werner, L., "E2F Proteins Regulate MYCN Expression in Neuroblastomas," *J. Biol. Chem. 278*:2983-2989, American Society for Biochemistry and Molecular Biology (Jan. 2003).
Takebe, A., "Microarray analysis of PDGFRα⁺ populations in ES cell differentiation culture identifies genes involved in differentiation of mesoderm and mesenchyme including ARID3b that is essential for development of embryonic mesenchymal cells," *Dev. Biol. 293*:25-37, Elsevier (May 2006).
International Search Report for International Application No. PCT/JP2006/325467, mailed on Jan. 30, 2007, Japanese Patent Office, Japan.
Database Espacenet, English language abstract for JP 2005-160354, 1 page (listed as document FP1 on accompanying form PTO/SB/08A), accessed Aug. 13, 2010 (2005).
Database Espacenet, English language abstract for JP 2005-304497, 1 page (listed as document FP2 on accompanying form PTO/SB/08A), accessed Aug. 13, 2010 (2005).
Burkhart, C.A. et al., "Effects of MYCN Antisense Oligonucleotide Administration on Tumorigenesis in a Murine Model of Neuroblastoma," *J. Natl. Cancer Inst. 95*:1394-1403, Oxford University Press (Sep. 17, 2003).
Weiss, W.A. et al., "Targeted expression of *MYCN* causes neuroblastoma in transgenic mice," *EMBO J.* 16:2985-2995, Oxford University Press (1997).
Supplementary European Search Report for European Patent Application No. 06842975.2, European Patent Office, Munich, Germany, mailed Oct. 28, 2009.
Written Opinion for European Patent Application No. 06842975.2, European Patent Office, Munich, Germany, mailed Oct. 28, 2009.

*Primary Examiner* — Brian Whiteman
(74) *Attorney, Agent, or Firm* — Sterne, Kessler, Goldstein & Fox P.L.L.C.

(57) ABSTRACT

It is intended to provide a therapeutic agent for neuroblastoma. More particularly, it is intended to provide the therapeutic agent for neuroblastoma containing an ARID3b inhibitor.

4 Claims, 5 Drawing Sheets

* p < 0.01 to the control

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic Antisense oligonucleotide for ARID3b
      designated as ARID3b AS1
<220> FEATURE:
<221> NAME/KEY: misc_feature
<222> LOCATION: (1)..(1)
<223> OTHER INFORMATION: 2'-O,4'-C-methylene bridged nucleic acids
      (BNAs)
<220> FEATURE:
<221> NAME/KEY: misc_feature
<222> LOCATION: (3)..(4)
<223> OTHER INFORMATION: 2'-O,4'-C-methylene bridged nucleic acids
      (BNAs)
<220> FEATURE:
<221> NAME/KEY: misc_feature
<222> LOCATION: (6)..(6)
<223> OTHER INFORMATION: 2'-O,4'-C-methylene bridged nucleic acids
      (BNAs)
<220> FEATURE:
<221> NAME/KEY: misc_feature
<222> LOCATION: (9)..(9)
<223> OTHER INFORMATION: 2'-O,4'-C-methylene bridged nucleic acids
      (BNAs)
<220> FEATURE:
<221> NAME/KEY: misc_feature
<222> LOCATION: (11)..(11)
<223> OTHER INFORMATION: 2'-O,4'-C-methylene bridged nucleic acids
      (BNAs)
<220> FEATURE:
<221> NAME/KEY: misc_feature
<222> LOCATION: (14)..(14)
<223> OTHER INFORMATION: 2'-O,4'-C-methylene bridged nucleic acids
      (BNAs)
<220> FEATURE:
<221> NAME/KEY: misc_feature
<222> LOCATION: (16)..(16)
<223> OTHER INFORMATION: 2'-O,4'-C-methylene bridged nucleic acids
      (BNAs)
<220> FEATURE:
<221> NAME/KEY: misc_feature
<222> LOCATION: (19)..(20)
<223> OTHER INFORMATION: 2'-O,4'-C-methylene bridged nucleic acids
      (BNAs)

<400> SEQUENCE: 1
gggttttcgg gcggcggagg                                              20

<210> SEQ ID NO 2
<211> LENGTH: 16
<212> TYPE: DNA
<213> ORGANISM: Artificial Sequence
<220> FEATURE:
<223> OTHER INFORMATION: Synthetic antisense oligonucleotide for ARID3b
      designated as ARID3b AS3
<220> FEATURE:
<221> NAME/KEY: misc_feature
<222> LOCATION: (2)..(2)
<223> OTHER INFORMATION: 2'-O,4'-C-methylene bridged nucleic acids
      (BNAs)
```

```
<220> FEATURE:
<221> NAME/KEY: misc_feature
<222> LOCATION: (4)..(5)
<223> OTHER INFORMATION: 2'-O,4'-C-methylene bridged nucleic acids
      (BNAs)
<220> FEATURE:
<221> NAME/KEY: misc_feature
<222> LOCATION: (8)..(8)
<223> OTHER INFORMATION: 2'-O,4'-C-methylene bridged nucleic acids
      (BNAs)
<220> FEATURE:
<221> NAME/KEY: misc_feature
<222> LOCATION: (10)..(11)
<223> OTHER INFORMATION: 2'-O,4'-C-methylene bridged nucleic acids
      (BNAs)
<220> FEATURE:
<221> NAME/KEY: misc_feature
<222> LOCATION: (13)..(13)
<223> OTHER INFORMATION: 2'-O,4'-C-methylene bridged nucleic acids
      (BNAs)
<220> FEATURE:
<221> NAME/KEY: misc_feature
<222> LOCATION: (16)..(16)
<223> OTHER INFORMATION: 2'-O,4'-C-methylene bridged nucleic acids
      (BNAs)

<400> SEQUENCE: 2
ctaaacctgt gcgggg                                                     16

<210> SEQ ID NO 3
<211> LENGTH: 20
<212> TYPE: DNA
<213> ORGANISM: Artificial Sequence
<220> FEATURE:
<223> OTHER INFORMATION: Synthetic Antisense oligonucleotide for ARID3b
      designated as ARID3b AS5
<220> FEATURE:
<221> NAME/KEY: misc_feature
<222> LOCATION: (1)..(8)
<223> OTHER INFORMATION: 2'-O,4'-C-methylene bridged nucleic acids
      (BNAs)
<220> FEATURE:
<221> NAME/KEY: misc_feature
<222> LOCATION: (11)..(13)
<223> OTHER INFORMATION: 2'-O,4'-C-methylene bridged nucleic acids
      (BNAs)
<220> FEATURE:
<221> NAME/KEY: misc_feature
<222> LOCATION: (20)..(20)
<223> OTHER INFORMATION: 2'-O,4'-C-methylene bridged nucleic acids
      (BNAs)

<400> SEQUENCE: 3 ccattttgc ctcaagcttc                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide designated as ARID3b
      AS5 scramble-1
<220> FEATURE:
<221> NAME/KEY: misc_feature
<222> LOCATION: (1)..(1)
<223> OTHER INFORMATION: 2'-O,4'-C-methylene bridged nucleic acids
      (BNAs)
<220> FEATURE:
<221> NAME/KEY: misc_feature
<222> LOCATION: (6)..(6)
<223> OTHER INFORMATION: 2'-O,4'-C-methylene bridged nucleic acids
      (BNAs)
<220> FEATURE:
<221> NAME/KEY: misc_feature
<222> LOCATION: (8)..(8)
<223> OTHER INFORMATION: 2'-O,4'-C-methylene bridged nucleic acids
```

```
      (BNAs)
<220> FEATURE:
<221> NAME/KEY: misc_feature
<222> LOCATION: (10)..(10)
<223> OTHER INFORMATION: 2'-O,4'-C-methylene bridged nucleic acids
      (BNAs)
<220> FEATURE:
<221> NAME/KEY: misc_feature
<222> LOCATION: (12)..(13)
<223> OTHER INFORMATION: 2'-O,4'-C-methylene bridged nucleic acids
      (BNAs)
<220> FEATURE:
<221> NAME/KEY: misc_feature
<222> LOCATION: (16)..(16)
<223> OTHER INFORMATION: 2'-O,4'-C-methylene bridged nucleic acids
      (BNAs)
<220> FEATURE:
<221> NAME/KEY: misc_feature
<222> LOCATION: (18)..(18)
<223> OTHER INFORMATION: 2'-O,4'-C-methylene bridged nucleic acids
      (BNAs)

<400> SEQUENCE: 4
gcttcccttc ttgcaacatt                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide designated as ARID3b
      AS5 scramble-2
<220> FEATURE:
<221> NAME/KEY: misc_feature
<222> LOCATION: (1)..(1)
<223> OTHER INFORMATION: 2'-O,4'-C-methylene bridged nucleic acids
      (BNAs)
<220> FEATURE:
<221> NAME/KEY: misc_feature
<222> LOCATION: (4)..(4)
<223> OTHER INFORMATION: 2'-O,4'-C-methylene bridged nucleic acids
      (BNAs)
<220> FEATURE:
<221> NAME/KEY: misc_feature
<222> LOCATION: (6)..(6)
<223> OTHER INFORMATION: 2'-O,4'-C-methylene bridged nucleic acids
      (BNAs)
<220> FEATURE:
<221> NAME/KEY: misc_feature
<222> LOCATION: (8)..(8)
<223> OTHER INFORMATION: 2'-O,4'-C-methylene bridged nucleic acids
      (BNAs)
<220> FEATURE:
<221> NAME/KEY: misc_feature
<222> LOCATION: (10)..(11)
<223> OTHER INFORMATION: 2'-O,4'-C-methylene bridged nucleic acids
      (BNAs)
<220> FEATURE:
<221> NAME/KEY: misc_feature
<222> LOCATION: (14)..(14)
<223> OTHER INFORMATION: 2'-O,4'-C-methylene bridged nucleic acids
      (BNAs)
<220> FEATURE:
<221> NAME/KEY: misc_feature
<222> LOCATION: (16)..(16)
<223> OTHER INFORMATION: 2'-O,4'-C-methylene bridged nucleic acids
      (BNAs)

<400> SEQUENCE: 5
gctgtaacca ccctttcttt                                              20

<210> SEQ ID NO 6
<211> LENGTH: 21
<212> TYPE: DNA
<213> ORGANISM: Artificial Sequence
<220> FEATURE:
```

```
<223> OTHER INFORMATION: Synthetic oligonucleotide designated as ARID3b
      RNAi(5) S
<220> FEATURE:
<221> NAME/KEY: misc_feature
<222> LOCATION: (20)..(21)
<223> OTHER INFORMATION: deoxyribonucleotides

<400> SEQUENCE: 6
ucaccaaagg ccuaaaccut t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide designated as ARID3b
      RNAi(5) A
<220> FEATURE:
<221> NAME/KEY: misc_feature
<222> LOCATION: (20)..(21)
<223> OTHER INFORMATION: deoxyribonucleotides

<400> SEQUENCE: 7
agguuuaggc cuuuggugat t                                              21

<210> SEQ ID NO 8
<211> LENGTH: 1683
<212> TYPE: DNA
<213> ORGANISM: Homo sapiens

<400> SEQUENCE: 8
atggagccac ttcagcagca gcagcagcag cagcagcaac aacagaagca gccacacctg    60
gctcctctgc agatggatgc cagagagaag cagggccagc agatgagaga agcccagttc   120
ttgtatgccc aaaagctggt cacacagccg actctccttt ccgccacagc tgggagacct   180
tctggcagca ctcccttagg tcccttagcc agagttccac ccaccgcagc agtggcccaa   240
gtgtttgaac ggggcaacat gaactcagag cctgaggaag aggacggagg tttggaagat   300
gaggatgggg atgatgaagt tgcagaggtg gctgagaaag aaacccaggc tgcttcaaaa   360
tattttcatg tgcagaaagt agctcgccaa gatcccagag tggcacccat gtccaatcta   420
cttccagcac cagggctccc accacatgga caacaagcta agaagaccta ccaaagat     480 gcttccaagg cctcaccttc tgtctccaca gcaggacagc cgaactggaa tctggatgag   540
cagctcaagc agaatggtgg tttggcctgg agtgatgatg cagatggagg ccggggaaga   600
gagatctctc gagattttgc caagctgtat gaactggacg tgatcctga aaggaaagag   660 ttcctggatg acctcttcgt ctttatgcag aagagggga cccccatcaa ccgaatcccc   720
atcatggcca acagatcct ggacctgtac atgctgtata agctggtgac cgagaaggga   780
ggcctggtgg agatcatcaa caagaagatc tggagggaga tcaccaaagg cctaaacctg   840
cccacatcca tcaccagcgc cgccttcacc ctcaggacgc agtacatgaa gtatctgtat   900
gcctatgagt gtgagaagaa agccttgagt tccccagccg agctccaggc agcaattgat   960
ggcaaccgca gggagggccg gcggcccagc tacagctcct ccctctttgg ctactcacct  1020
gctgcggcta ctgctgctgc cgctgccggg gcccctgccc ttctctcccc acccaagatc  1080
cgcttttcca tccttgggct tggctccagc agtggtacca ataccagtag ccctcggata  1140
tccccagcaa ccactctcag gaaaggtgat ggagcccag tgacaacagt gcctgtgcca  1200
aatcgtctgg ctgtgcccgt gaccttggca agcagcagg ctggtactcg gaccgccgca  1260
ctggagcagc tgcgggagcg gctggagtca ggggagcctg ctgagaagaa ggcatcgagg  1320
```

```
ctgtctgagg aggagcagcg cctggtgcag caggccttcc agcgcaactt tttcagcatg    1380
gcacggcagc tccccatgaa gatcaggatc aacggcaggg aagacagagc agaggcctcg    1440
gctgcagcac tgaacctgac cacgagtagc attgggagca ttaacatgtc tgtggacatc    1500
gatggcacca cctatgcagg tgtgctgttt gcccagaagc ctgtggtcca cctcatcacg    1560
gggtctgctc cccagagcct cggcagcagc gccagcagca gcagcagctc tcactgttca    1620
ccaagtccta cctcatcccg gggcaccccc agcgcagagc cctccaccag ctggtccctc    1680
tga                                                                  1683
```

<210> SEQ ID NO 9
<211> LENGTH: 560
<212> TYPE: PRT
<213> ORGANISM: Homo sapiens

<400> SEQUENCE: 9

```
Met Glu Pro Leu Gln Gln Gln Gln Gln Gln Gln Gln Gln Gln Gln Lys
  1               5                  10                  15

Gln Pro His Leu Ala Pro Leu Gln Met Asp Ala Arg Glu Lys Gln Gly
                 20                  25                  30

Gln Gln Met Arg Glu Ala Gln Phe Leu Tyr Ala Gln Lys Leu Val Thr
             35                  40                  45

Gln Pro Thr Leu Leu Ser Ala Thr Ala Gly Arg Pro Ser Gly Ser Thr
         50                  55                  60

Pro Leu Gly Pro Leu Ala Arg Val Pro Pro Thr Ala Ala Val Ala Gln
 65                  70                  75                  80

Val Phe Glu Arg Gly Asn Met Asn Ser Glu Pro Glu Glu Asp Gly
                 85                  90                  95

Gly Leu Glu Asp Glu Asp Gly Asp Asp Glu Val Ala Glu Val Ala Glu
                100                 105                 110

Lys Glu Thr Gln Ala Ala Ser Lys Tyr Phe His Val Gln Lys Val Ala
            115                 120                 125

Arg Gln Asp Pro Arg Val Ala Pro Met Ser Asn Leu Leu Pro Ala Pro
        130                 135                 140

Gly Leu Pro Pro His Gly Gln Gln Ala Lys Glu Asp His Thr Lys Asp
145                 150                 155                 160

Ala Ser Lys Ala Ser Pro Ser Val Ser Thr Ala Gly Gln Pro Asn Trp
                165                 170                 175

Asn Leu Asp Glu Gln Leu Lys Gln Asn Gly Gly Leu Ala Trp Ser Asp
                180                 185                 190

Asp Ala Asp Gly Gly Arg Gly Arg Glu Ile Ser Arg Asp Phe Ala Lys
            195                 200                 205

Leu Tyr Glu Leu Asp Gly Asp Pro Glu Arg Lys Glu Phe Leu Asp Asp
        210                 215                 220

Leu Phe Val Phe Met Gln Lys Arg Gly Thr Pro Ile Asn Arg Ile Pro
225                 230                 235                 240

Ile Met Ala Lys Gln Ile Leu Asp Leu Tyr Met Leu Tyr Lys Leu Val
                245                 250                 255

Thr Glu Lys Gly Gly Leu Val Glu Ile Ile Asn Lys Lys Ile Trp Arg
                260                 265                 270

Glu Ile Thr Lys Gly Leu Asn Leu Pro Thr Ser Ile Thr Ser Ala Ala
            275                 280                 285

Phe Thr Leu Arg Thr Gln Tyr Met Lys Tyr Leu Tyr Ala Tyr Glu Cys
        290                 295                 300

Glu Lys Lys Ala Leu Ser Ser Pro Ala Glu Leu Gln Ala Ala Ile Asp
```

```
305                 310                 315                 320
Gly Asn Arg Arg Glu Gly Arg Arg Pro Ser Tyr Ser Ser Ser Leu Phe
                325                 330                 335
Gly Tyr Ser Pro Ala Ala Ala Thr Ala Ala Ala Ala Gly Ala Pro
            340                 345                 350
Ala Leu Leu Ser Pro Pro Lys Ile Arg Phe Pro Ile Leu Gly Leu Gly
        355                 360                 365
Ser Ser Ser Gly Thr Asn Thr Ser Ser Pro Arg Ile Ser Pro Ala Thr
        370                 375                 380
Thr Leu Arg Lys Gly Asp Gly Ala Pro Val Thr Thr Val Pro Val Pro
385                 390                 395                 400
Asn Arg Leu Ala Val Pro Val Thr Leu Ala Ser Gln Gln Ala Gly Thr
            405                 410                 415
Arg Thr Ala Ala Leu Glu Gln Leu Arg Glu Arg Leu Glu Ser Gly Glu
            420                 425                 430
Pro Ala Glu Lys Lys Ala Ser Arg Leu Ser Glu Glu Glu Gln Arg Leu
        435                 440                 445
Val Gln Gln Ala Phe Gln Arg Asn Phe Phe Ser Met Ala Arg Gln Leu
450                 455                 460
Pro Met Lys Ile Arg Ile Asn Gly Arg Glu Asp Arg Ala Glu Ala Ser
465                 470                 475                 480
Ala Ala Ala Leu Asn Leu Thr Thr Ser Ser Ile Gly Ser Ile Asn Met
            485                 490                 495
Ser Val Asp Ile Asp Gly Thr Thr Tyr Ala Gly Val Leu Phe Ala Gln
            500                 505                 510
Lys Pro Val Val His Leu Ile Thr Gly Ser Ala Pro Gln Ser Leu Gly
        515                 520                 525
Ser Ser Ala Ser Ser Ser Ser Ser His Cys Ser Pro Ser Pro Thr
        530                 535                 540
Ser Ser Arg Gly Thr Pro Ser Ala Glu Pro Ser Thr Ser Trp Ser Leu
545                 550                 555                 560
```

THERAPEUTIC AGENT FOR NEUROBLASTOMA TARGETING ARID3B

TECHNICAL FIELD

The present invention relates to a composition for treating neuroblastoma which contains an ARID3b inhibitor.

BACKGROUND ART

Neuroblastoma is a disease that frequently occurs principally in children of five years old or younger, and of which the frequency is the highest among solid tumors in infants. As to genetic features associated with neuroblastoma, amplification of MYCN oncogene, deletion of chromosome 1p and the like are known. In particular, the current therapy is not effective for many of cases of patients of one year old or older having highly advanced tumors, or cases with the above-mentioned amplification of MYCN oncogene or deletion of chromosome 1p. Although the relationship between the amplification of MYCN oncogene (found in about 20% of the disease cases) and neuroblastoma was suggested in the mid-1980s, there has been no report on a molecule that surely has an important function specific for neuroblastoma since then, and almost nothing has been elucidated concerning the molecular mechanism of the tumor. Although there is an urgent need for establishment of a method of treating neuroblastoma, the above has been a principal cause that impedes development of a new treatment method (Non-patent Document 1).

The present inventors produced an ARID3b knock-out (KO) mouse during the course of studies on differentiation-induction of mesodermal cells and mesenchymal cells using an in vitro differentiation system for mouse embryonic stem (ES) cells. ARID3b is a molecule of unknown function of which the expression pattern is similar to that of platelet-derived growth factor (PDGF) receptor molecule. Based on the observation that most of PDGFRα-positive cranial mesenchymal cells which were considered to be derived from neural crest cells disappeared in the KO mouse, it was found that this molecule is indispensable for differentiation, growth and maintenance of mesenchymal cells. The ADID3b molecule is a protein that belongs to a group of molecules that have a DNA-binding motif called AT rich interacting domain. The gene encoding this protein forms a subfamily with another gene for ARID3a. The gene encoding human ARID3b was cloned, and ARID3b was shown to be a protein that binds to retinoblastoma gene product (Rb) (Non-patent Document 2), although its function has been unknown.

Non-patent Document 1: Brodeur, G. M. et al., Nature Reviews Cancer, 3:203-216 (2003)
Non-patent Document 2: Numata, S. et al., Cancer Res., 59:3741-3747 (1999)

DISCLOSURE OF INVENTION

Problems to be Solved by the Invention

The main object of the present invention is to provide a composition for treating neuroblastoma.

Means to Solve the Problems

The present inventors have found during the course of studies using the above-mentioned KO mouse and the like that ARID3b molecule is expressed in cranial mesenchymal cells, and is important for their survival. The present inventors have further found that ARID3b molecule is expressed in neuroblastoma cell lines with high frequency, and is involved in canceration of cells. Thus, the present invention has been completed.

The present invention relates to the following:

[1] A composition for treating neuroblastoma, which contains an ARID3b inhibitor;

[2] The composition according to [1], wherein the ARID3b inhibitor is an antisense oligonucleotide or an siRNA for ARID3b mRNA;

[3] A method of screening for an ARID3b inhibitor, the method comprising measuring an activity of inhibiting ARID3b;

[4] The method according to [3], wherein the activity of inhibiting ARID3b is an activity of inhibiting expression of ARID3b;

[5] The method according to [3], wherein the activity of inhibiting ARID3b is an activity of inhibiting an action of ARID3b;

[6] A method of suppressing neuroblastoma, the method comprising inhibiting ARID3b;

[7] The method according to [6], wherein ARID3b is inhibited by inhibiting expression of ARID3b;

[8] The method according to [6], wherein ARID3b is inhibited by inhibiting an action of ARID3b;

[9] A method of diagnosing neuroblastoma, the method comprising measuring an expression level of ARID3b in a cell;

[10] The method according to [9], which further comprises measuring an expression level of MYCN in a cell;

[11] A cell in which expression of ARID3b is modified;

[12] An animal in which expression of ARID3b is modified;

[13] A kit for determining neuroblastoma, which contains at least an antibody against ARID3b or an oligonucleotide that is capable of annealing to an ARID3b-encoding gene or a sequence complementary thereto;

[14] The kit according to [13], wherein the oligonucleotide contains a sequence of consecutive 15 to 100 nucleotides selected from an ARID3b-encoding gene or a sequence complementary thereto;

[15] The kit according to [13], which further contains an antibody against MYCN or an oligonucleotide that is capable of annealing to an MYCN-encoding gene or a sequence complementary thereto.

Effects of the Invention

The present invention provides a composition for treating neuroblastoma which contains an ARID3b inhibitor.

BEST MODE FOR CARRYING OUT THE INVENTION

Figure 1A:
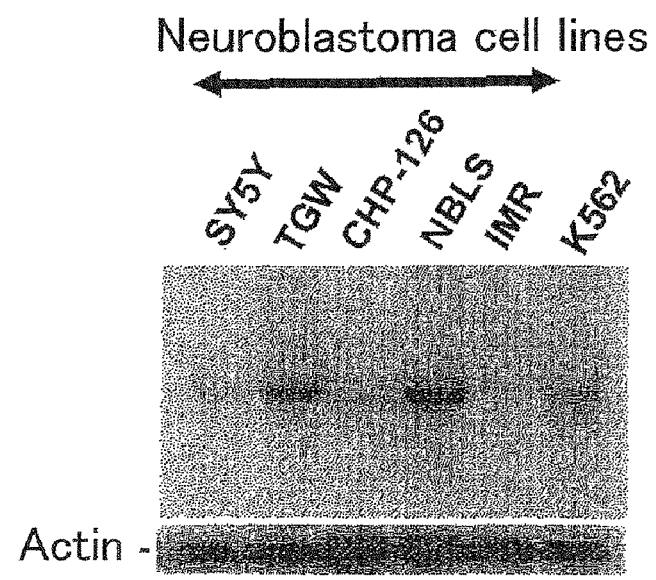
FIG. 1A illustrates expression of ARID3b mRNA in neuroblastoma cell lines.

As used herein, neuroblastoma refers to malignant tumor of an undifferentiated cell that differentiates to a neural cell (neuroblast). Furthermore, as used herein, a neuroblastoma cell line refers to a cell line that is derived from neuroblastoma and exhibits a characteristic of neuroblastoma. Examples of neuroblastoma cell lines include SH-SY5Y, TGW, CHP-126, NBLS and IMR.

ARID3b protein (ARID3b molecule) is a protein that belongs to a group of molecules that have a DNA-binding motif called AT rich interacting domain and binds to retinoblastoma gene product (Rb). The expression pattern of ARID3 gene is similar to that of platelet-derived growth factor (PDGF) receptor molecule. For example, the amino acid sequence of human ARID3b protein and the nucleotide sequence of the gene encoding the same are disclosed in Non-patent Document 2 and registered at GenBank under accession number NM_006465. The sequence of the coding region in the nucleotide sequence of human ARID3b gene available from GenBank accession number NM_006465 and the amino acid sequence encoded by the nucleotide sequence are shown in SEQ ID NOS:8 and 9, respectively.

The present inventors have shown that expression levels of ARID3b mRNA are increased in neuroblastoma cell lines, and that the growth of a neuroblastoma cell line is suppressed and the malignancy is decreased by allowing an antisense oligonucleotide, an siRNA or the like to act on ARID3b mRNA. Thus, it is considered that expression of ARID3b is involved in at least a part of neuroblastomas, and such neuroblastomas can be treated by inhibiting ARID3b. The disease stages of neuroblastoma are classified into stage I, stage IIa, stage II (IIb), stage III, stage IV and stage IVs according to the International Neuroblastoma Staging System (INSS) that represents the degree of progress. Since correlation between ARID3b expression and stage IV is observed, it is possible that inhibition of ARID3b is particularly effective against neuroblastoma at stage IV. Furthermore, since forced expression of ARID3b in primary cultured fibroblasts results in canceration of the normal cells, it is possible that inhibition of ARID3b is effective also for treatment of cancers other than neuroblastoma.

In one embodiment, the present invention provides a composition for treating neuroblastoma which contains an ARID3b inhibitor, a method of screening for an ARID3b inhibitor comprising measuring an activity of inhibiting ARID3b, and a method of suppressing neuroblastoma comprising inhibiting ARID3b. As used herein, an ARID3b inhibitor refers to a substance that has an activity of inhibiting ARID3b. The activity of inhibiting ARID3b may be either an activity of inhibiting expression of ARID3b or an activity of inhibiting an action of ARID3b.

As used herein, expression encompasses transcription of a gene into an mRNA and translation of an mRNA into a protein. The inhibition of expression according to the present invention encompasses inhibition of expression at the transcriptional level and inhibition of expression at the translational level. Thus, the ARID3b inhibitor which has an activity of inhibiting expression of ARID3b may be any substance that inhibits transcription into ARID3b mRNA or translation into ARID3b protein.

ARID3b inhibitors include antisense oligonucleotides, siRNAs and ribozymes for ARID3b mRNA. Alternatively, a substance that acts on a transcription regulatory system for ARID3b gene to inhibit transcription into ARID3b mRNA can be used according to the present invention. For example, such a substance can be obtained by treating an ARID3b-expressing cell line with test substances and selecting a substance that decreases the amount of ARID3b mRNA or the amount of ARID3b protein, or a substance that suppresses the growth of the cell line. As an ARID3b-expressing cell line, the above-mentioned neuroblastoma cell line or a cell in which expression of ARID3b is modified as described below can be used. Methods for obtaining antisense oligonucleotides, siRNAs and ribozymes are known in the art. Those skilled in the art can readily obtain them, for example, based on the above-mentioned nucleotide sequence of human ARID3b gene.

ARID3b protein is known to bind to Rb. Furthermore, it has been shown by the present inventors, using increases in growth ability and colony formation ability as indexes, that high expression of ARID3b results in increased malignancy of a neuroblastoma cell line. Thus, an activity of inhibiting an action of ARID3b can be confirmed based on ability of ARID3b protein to bind to Rb, suppression of growth ability of a cell, or the like. For example, a substance that binds to ARID3b protein or Rb to inhibit the binding of ARID3b protein to Rb can be used as an ARID3b inhibitor. Thus, antibodies against ARID3b protein obtained using conventional methods (including polyclonal antibodies, monoclonal antibodies and antibody fragments) can be used as ARID3b inhibitors.

The method of suppressing neuroblastoma of the present invention comprises inhibiting ARID3b. For example, this method is effective in studying the function of ARID3b protein or elucidating the mechanism of neuroblastoma onset. As described above, ARID3b is inhibited by inhibiting expression or an action of ARID3b, for example, by in vivo or in vitro addition or administration of an ARID3b inhibitor. Subjects include mammals (including human or not including human) and cells derived from mammals.

In another embodiment, the present invention provides a method of diagnosing neuroblastoma comprising measuring an expression level of ARID3b in a cell. As described above, expression of ARID3b is involved in at least a part of neuroblastomas. Therefore, it is possible to characterize neuroblastoma based on higher ARID3b expression as compared with that in normal cells by measuring the amount of ARID3b mRNA or a translation product thereof (ARID3b protein). The amount of ARID3b mRNA can be measured using a method known in the art such as Northern blot hybridization or quantitative RT-PCR. A probe for detection, a primer for amplification or the like to be used in such a method can be designed, for example, based on the nucleotide sequence of SEQ ID NO:8. The amount of ARID3b protein can be measured using a method known in the art such as ELISA or immunohistochemical staining using an antibody, which is prepared according to a conventional method, against ARID3b protein having the amino acid sequence of SEQ ID NO:9 or a part thereof. Examination of expression of ARID3b and MYCN in various tumors has shown that determination as neuroblastoma is highly possible if expression of both ARID3b and MYCN oncogene is detected. Thus, it is possible to diagnose neuroblastoma more accurately by measuring an expression level of MYCN in addition to ARID3b. An expression level of MYCN can be measured by determining the amount of the transcription product (MYCN mRNA) or the translation product (MYCN protein) of MYCN oncogene. Furthermore, since correlation between ARID3b expression and neuroblastoma at stage IV is observed as described above, it is possible to diagnose the disease stage of neuroblastoma by measuring an expression level of ARID3b.

In another embodiment, the present invention provides a cell in which expression of ARID3b is modified and an animal in which expression of ARID3b is modified. It has been found by the present inventors that malignancy of a cell is increased and a primary cultured cell is immortalized by enhancing (forcing) expression of ARID3b in a neuroblastoma cell line and a primary cultured cell. Thus, malignancy of a cell can be modified by artificially modifying expression of ARID3b in the cell. As used herein, modifying expression refers to decreasing or increasing the expression level as compared with the inherent one, enabling expression regulation that is different from the inherent one, or the like. For example, expression of ARID3b can be modified by introducing a vector for expressing ARID3b protein, introducing a vector for expressing an antisense for ARID3b mRNA, or altering an expression regulatory region for ARID3b gene of a host cell. Recombinant DNA techniques used for such a procedure including construction of an expression vector and introduction of the same into a cell are known in the art. Furthermore, it is possible to obtain an animal in which expression of ARID3b is modified by making a transgenic animal, a clone animal or the like from a germ cell or a somatic cell in which expression of ARID3b is modified according to a conventional method. Such a cell or an animal is useful in screening for an ARID3b inhibitor, studying the function of ARID3b protein, elucidating the mechanism of neuroblastoma onset, and the like.

In a further embodiment, the present invention provides a kit for determining neuroblastoma, which contains at least an antibody against ARID3b, or an oligonucleotide that is capable of annealing to an ARID3b-encoding gene or a sequence complementary thereto. This kit can be used for the above-mentioned method of diagnosing neuroblastoma. The above-mentioned antibody can be used as the antibody against ARID3b. There is no specific limitation concerning the form of the ARID3b-encoding gene or a sequence complementary thereto that is to be subjected to detection or amplification. For determining neuroblastoma based on expression at the transcriptional level, it is preferably mRNA. The oligonucleotide that is capable of annealing to an ARID3b-encoding gene or a sequence complementary thereto may be either a probe for detection or a primer for amplification, and it may be DNA, RNA or a mixture thereof (chimeric oligonucleotide). There is no specific limitation concerning the length of the oligonucleotide as long as the oligonucleotide is capable of specifically annealing to an ARID3b-encoding gene or a sequence complementary thereto. For example, the oligonucleotide contains a sequence of consecutive 10 nucleotides or more, preferably 15 nucleotides or more, more preferably 20 nucleotides or more, still more preferably 25 nucleotides or more, and 500 nucleotides or less, preferably 200 nucleotides or less, more preferably 100 nucleotides or less, still more preferably 50 nucleotides or less selected from an ARID3b-encoding gene or a sequence complementary thereto. For example, an oligonucleotide that contains a sequence of consecutive 15 to 100 nucleotides selected from an ARID3b-encoding gene or a sequence complementary thereto can be preferably used. Conditions for annealing (hybridization) of an oligonucleotide to an ARID3b-encoding gene or a sequence complementary thereto are known in the art, and described, for example, in J. Sambrook et al. (eds.), Molecular Cloning: A Laboratory Manual 3rd ed., 2001, Cold Spring Harbor Laboratory Press. The kit of the present invention may further contain an antibody against MYCN, or an oligonucleotide that is capable of annealing to an MYCN-encoding gene or a sequence complementary thereto.

The following Examples illustrate the present invention in more detail, but are not to be construed to limit the scope thereof.

Example 1

Expression of ARID3b mRNA was examined for five neuroblastoma cell lines. SH-SY5Y (ATCC CRL-2266), TGW (Iwasaki, I. et al., Cancer Chemother. Pharmacol., 49:438-444 (2002)), CHP-126 (Schlesinger, H. R. et al., Cancer Res., 36:3094-3100 (1976)), NBLS and IMR (ATCC CCL-127) were used as neuroblastoma cell lines. Furthermore, K562 (chronic myelogenous leukemia, ATCC CCL-243) was used as a control. A medium consisting of 45% Dulbecco's minimum essential medium (D-MEM, Invitrogen), 45% Ham's F-12 medium (Invitrogen) and 10% fetal bovine serum (FES, JRL) was used for the cultivation of neuroblastoma cell lines. A medium consisting of 90% D-MEM and 10% FBS was used for other cell lines. RNA was extracted from each cell line according to a conventional method, and subjected to Northern blot hybridization using human ARID3b DNA (SEQ ID NO:8) as a probe. Detection of actin mRNA was carried out in a similar manner. The results are shown in FIG. 1A. As shown in FIG. 1A, although the expression levels of ARID3b mRNA varied depending on the cell lines, bands of about 4.2 kbp which represent the expression of ARID3b mRNA were observed for all of the neuroblastoma cell lines.

Figure 1B:
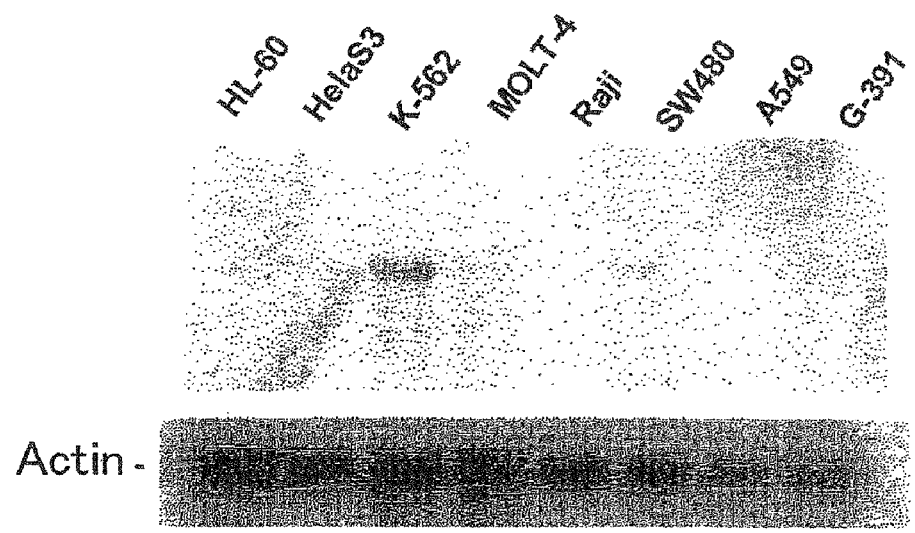
FIG. 1B illustrates expression of ARID3b mRNA in various cancer cell lines.

Similarly, expression of ARID3b mRNA was examined for cell lines from cancers other than neuroblastoma. HL-(acute promyelocytic leukemia, ATCC CCL-240), HeLa S3 (cervical cancer, ATCC CCL-2.2), K-562 (chronic myelogenous leukemia, ATCC CCL-243), MOLT-4 (acute lymphoblastic leukemia, ATCC CRL-1582), Raji (L3, Burkitt's lymphoma, ATCC CCL-86), SW480 (colon cancer, ATCC CCL-228), A549 (lung cancer, ATCC CCL-185) and G-391 (melanoma) were used as cell lines. The results are shown in FIG. 1B. Bands of about 4.2 kbp which represent the expression of ARID3b mRNA were observed for the chronic myelogenous leukemia line K-562 and the colon cancer cell line SW480, while the expression was not observed for other cell lines. Thus, the frequency of expression was lower than that for the above-mentioned neuroblastoma cell lines.

Based on these results, it was shown that ARID3b mRNA was significantly expressed in neuroblastoma cell lines.

Example 2

Figure 2A:
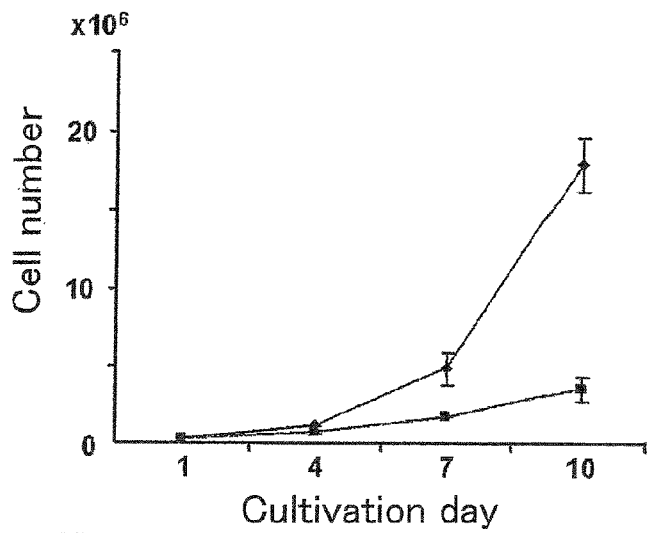
FIG. 2A illustrates influence of forced expression of ARID3b on growth ability.

Influence of forced expression of ARID3b on in vitro malignancy of a cell was examined using growth ability and colony formation ability as indexes. A retrovirus having human ARID3b DNA (SEQ ID NO:8) being inserted was constructed. The retrovirus contained in MSCV Retrovirus Expression System (Cat. No. 634401) which is commercially available from Clontech was used as a retrovirus after substituting IRES GFP for the drug resistance gene portion. This recombinant retrovirus was used to infect the neuroblastoma cell line SH-SY5Y to forcibly express ARID3b and the cell number was measured over time. For SH-SY5Y, expression of ARID3b was observed in Example 1, and it was known that amplification of MYCN oncogene is not found. The results are shown in FIG. 2A. In the figure, diamonds (♦) represent results of infection with the retrovirus having ARID3b DNA being inserted, and squares (|) represent results of infection with the vector without the insert DNA. As shown in FIG. 2A, the cell subjected to the forced expression exhibited higher growth ability as compared with the cell without the forced expression.

Figure 2B:
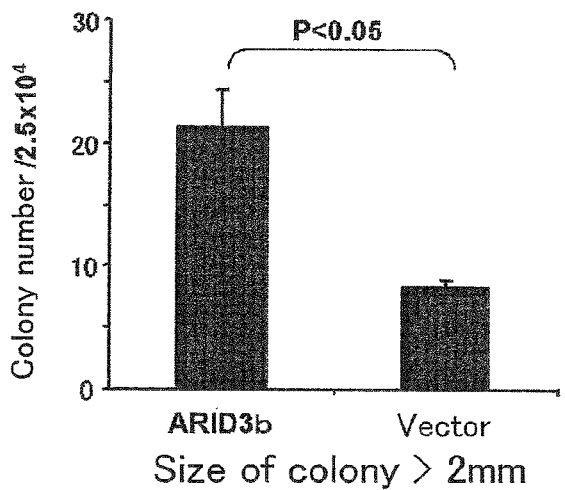
FIG. 2B illustrates influence of forced expression of ARID3b on colony formation ability.
Figure 2C:
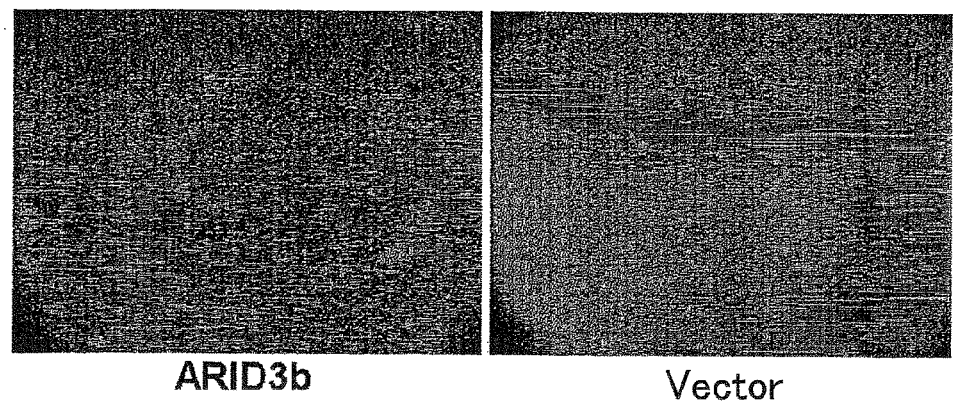
FIG. 2C illustrates influence of forced expression of ARID3b on colony formation ability.

Colonies (greater than 2 mm in diameter) formed by the cells were counted. The results are shown in FIGS. 2B and 2C. As shown in FIGS. 2B and 2C, the colony formation ability was significantly increased when ARID3b was forcibly expressed as compared with the case of vector alone.

Figure 3:
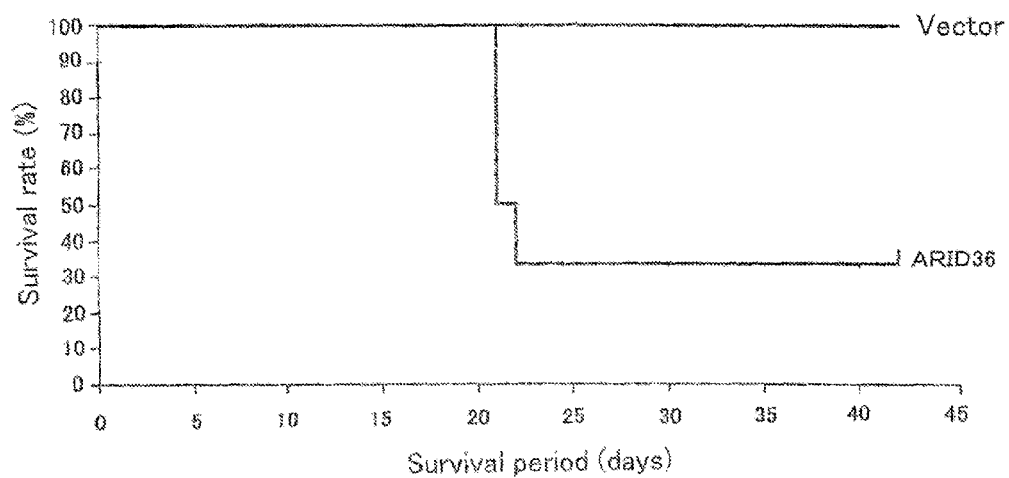
FIG. 3 illustrates survival rates of immunodeficient mice after cell transplantation.

Furthermore, in vivo malignancy was examined by subcutaneously transplanting the above-mentioned respective cells independently into immunodeficient mice, and measuring survival rates of the mice after transplantation over time. A Kaplan-Meier survival curve which represents the results is shown in FIG. 3. As shown in FIG. 3, almost no death of the mice was observed in the case of vector alone over the test period. On the other hand, death was observed within a short period of time (about 20 days) for the immunodeficient mice transplanted with SH-SY5Y cells subjected to the forced expression of ARID3b.

Based on these results, it was shown that forced expression of ARID3b increases in vitro and in vivo malignancy of a neuroblastoma cell line.

Example 3

Figure 4:
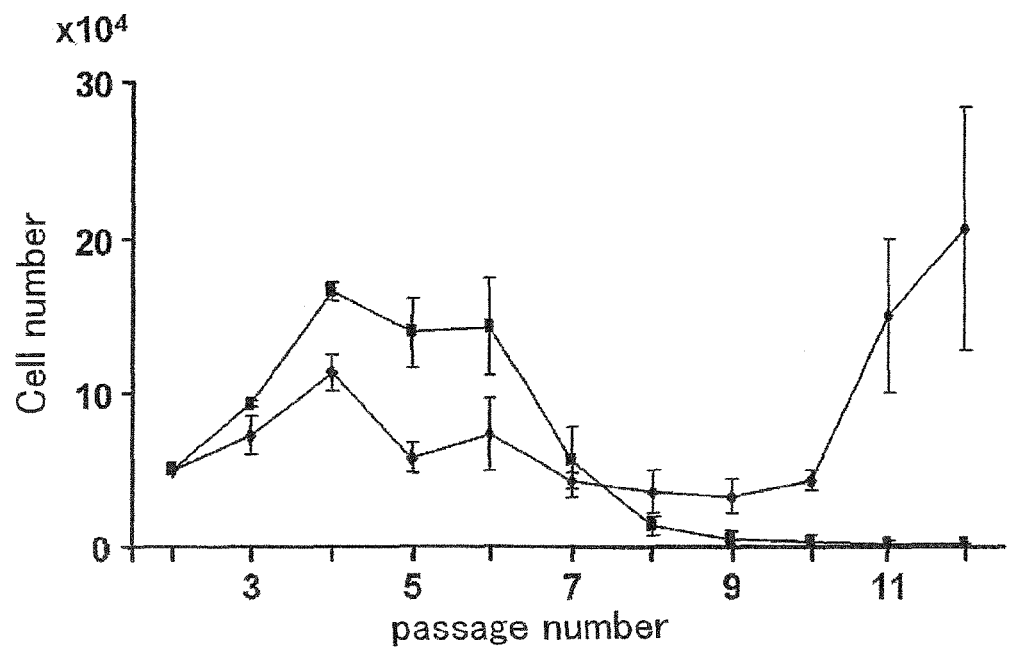
FIG. 4 illustrates influence of forced expression of ARID3b on canceration of primary cultured cells.

Influence of forced expression of ARID3b on canceration of a primary cultured cell was examined using senescence and immortalization during passage cultures as indexes. The retrovirus having human ARID3b DNA being inserted used in Example 2 was used to infect mouse primary cultured fibroblasts isolated from a fetus. A medium consisting of 90% D-MEM and 10% FBS was used for the cultivation of primary cultured fibroblasts. The cells were passaged at intervals of two or three days by washing with Dulbecco's phosphate-buffered saline (PBS, Invitrogen), detaching from dishes using 0.05% (w/v) trypsin-EDTA (Invitrogen), and diluting 5-fold. The cells were counted upon passages. The results are shown in FIG. 4. In the figure, diamonds (♦) represent results of infection with the retrovirus having ARID3b DNA being inserted and squares (|) represent results of infection with the vector without the insert DNA. As shown in FIG. 4, when the primary cultured fibroblasts infected with the vector alone were passaged eight times or more, an arrest of division probably due to senescence and cell death associated therewith were observed, and further passage was difficult. On the other hand, although the primary cultured fibroblasts subjected to the forced expression of ARID3b exhibited lower growth ability at the beginning of the cultivation after introduction of the retrovirus as compared with the control of the vector alone, the growth ability was increased thereafter and maintenance culture was possible for three months or more.

Based on these results, it was suggested that the forced expression of ARID3b suppressed senescence of a primary cultured cells, caused immortalization, and promoted canceration.

Example 4

Influence of suppression of ARID3b expression in a neuroblastoma cell line on the growth was examined.

CHP-126S, for which low expression of ARID3b mRNA was confirmed in Example 1, was used as a neuroblastoma cell line. Antisense oligonucleotides ARID3b AS1 (AS1, SEQ ID NO:1), ARID3b AS3 (AS3, SEQ ID NO:2) and ARID3b AS5 (AS5, SEQ ID NO:3) were synthesized. Furthermore, oligonucleotides ARID3b AS5 scramble-1 (scramble-1, SEQ ID NO:4) and ARID3b AS5 scramble-2 (scramble-2, SEQ ID NO:5) having sequences in which the sense sequence of AS5 was randomly rearranged were synthesized as controls. 2'-O,4'-C-methylene bridged nucleic acid (BNA) was partially used for the syntheses of the respective oligonucleotides. In addition, ARID3b RNAi(5)S (sense) (SEQ ID NO:6) and ARID3b RNAi(5)A (antisense) (SEQ ID NO:7) were synthesized and then annealed to each other to form an siRNA.

$3 \times 10^4$ cells in 100 μl of a medium were seeded into a 96-well plate. After 24 hours, 0.2 μg of one of the oligonucleotides or PBS (mock) was introduced using Lipofectamine 2000 (Invitrogen) in Opti-MEM medium (Gibco, Invitrogen Corporation United Kingdom) according to the manufacturer's instructions. After 24 hours, the medium was exchanged for a normal medium for neuroblasts, the culture was diluted 4-fold, and the cells were cultivated for three days. After cultivating for three days, an equal volume of CellTiter-Glo Reagent (CellTiter-Glo™ Luminescent Cell Viability Assay; Promega catalog no. G7571) was added to the culture medium, the mixture was allowed to stand for ten minutes at room temperature, and the absorbance was then measured using Luminometer (Lumat LB 9507 Berthold Technology). Growth ratios were calculated as ratios of the ATP values after cultivation for three days to the ATP values for cells before introduction of the oligos. Similar growth experiments can be carried out by counting the cell number under a microscope.

Figure 5A:
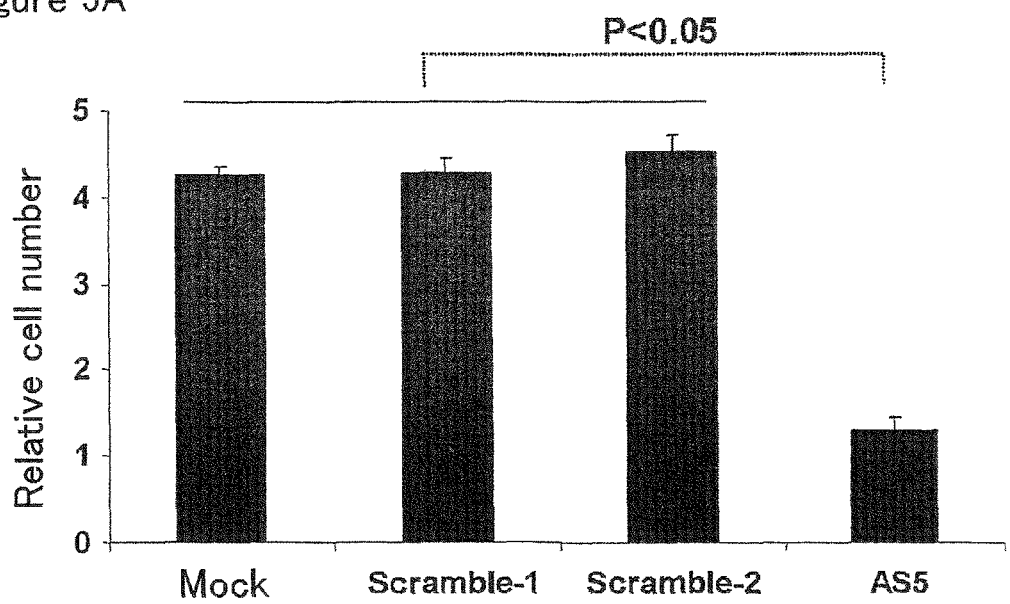
FIG. 5A illustrates influence of an antisense oligonucleotide for ARID3b on growth of neuroblastoma cell lines.

Results of experiments using the antisense oligonucleotides are shown in FIG. 5A. As shown in FIG. 5A, when the antisense oligonucleotide AS5 for ARID3b mRNA was introduced into the neuroblastoma cell line CHP-126, significant growth suppression was observed as compared with the mock, or scramble-1 or scramble-2 as a control. In particular, AS5 suppressed the growth of the cell line. Similar experiments can be carried out using the antisense oligonucleotide ARID3b AS1 (AS1, SEQ ID NO:1) or ARID3b AS3 (AS3, SEQ ID NO:2).

Figure 5B:
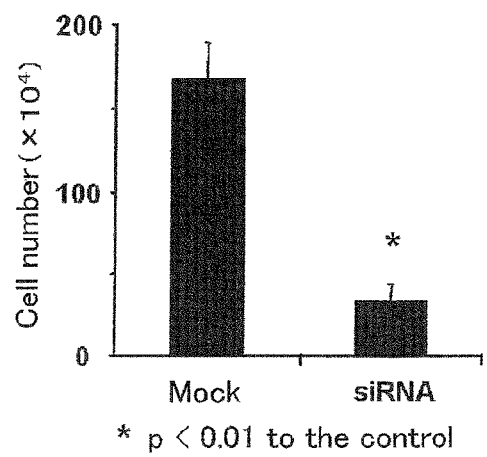
FIG. 5B illustrates influence of an siRNA for ARID3b on growth of a neuroblastoma cell line.

Results of experiments in which the siRNA was introduced into CHP-126 cells are shown in FIG. 5B. Like the case of the antisense oligonucleotide, a significant growth-suppressive effect was observed when the siRNA for ARID3b mRNA was introduced.

Figure 5C:
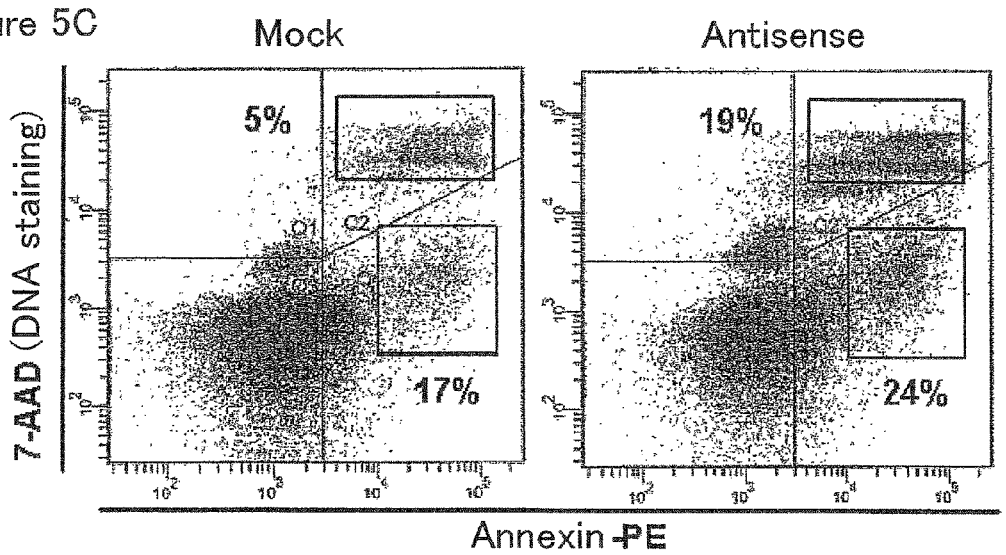
FIG. 5C illustrates the relationship between growth suppression by an antisense oligonucleotide and apoptosis induction.

The growth-suppressive effect of the antisense oligonucleotide AS5 on CHP-126 cells was examined by flow cytometry analysis after staining the cells with 7-aminoactinomycin D (7-AAD), which is a DNA-staining dye which represents cell growth, and phycoerythrin-conjugated annexin (annexin-PE), which represents cells undergoing apoptosis. The results are shown in FIG. 5C. As shown in FIG. 5C, increase in cells undergoing apoptosis was observed for the cells into which the antisense oligonucleotide had been introduced. That is, it was suggested that the growth-suppressive effect of the antisense oligonucleotide on the neuroblastoma cell line was caused by apoptosis induction, and ARID3b plays an important role in growth of the neuroblastoma cell.

Example 5

Expression of ARID3b and MYCN in various tumors was examined. Expression data were obtained from ArrayExpress (Parkinson, H. et al., Nucleic Acids Res., 33 (Database issue): D553-555 (2005)) and NCBI Gene Expression Omnibus (Edgar, R. et al., Nucleic Acids Res., 30:207-210 (2002)).

Affymetrix detection calls were calculated from raw data using affy module in bioconductor suite (Gentleman, R. C. et al., Genome Biol., 5:R80 (2004)). The normal group was composed of 602 samples. Although they were obtained from a wide variety of different tissues and cell types, they were processed as a single group in the analysis. The respective samples were classified according to the tumor types. Depending on the information available from the respective data suppliers, the accuracy of tumor classification may vary among the tumor sets. The expression sample number was counted judging "present" and "marginal" calls as "detected". For indicating the probability of finding at least the positive (detected) sample number counted for each tumor type, p value was calculated using hypergeometric distribution. The p value depends on both the ratio of positive samples and the sample number for the tumor type. The p value is within a range of 0 to 1. A value close to 1 represents non-specific expression, and a value close to 0 represents specific expression. A case was determined to show a significant relationship when the p value was less than 0.0019 (0.05/26 (number of tumor types)). Expression of MYCN and ARID3b was examined using probe sets 209757_s_at and 218964_at, respectively. The results are shown in Table 1.

Example 5, are reported in detail, use highly standardized Affymetrix oligonucleotide array, and therefore enable extraction of related data and comparison with another data set. Twenty-three malignant neuroblastoma samples were examined. Two of them were neuroblastoma cell lines, and others were from neuroblastoma at stage I (one sample), stage IIa (two samples), stage II (six samples), stage III (one sample), stage IV (ten samples) and stage IVs (one sample). ARID3b was determined to be "detected" in 11 out of 23 samples based on the "present" or "marginal" calls. Two of them were neuroblastoma cell lines, one sample was from neuroblastoma at stage II, and the remaining eight samples were from neuroblastoma at stage IV. Expression of ARID3b was observed for 9 out of 21 (42.8%) neuroblastoma cases (excluding the two cell lines). In particular, the expression was correlated with the tumor at stage IV (8 out of 10 (80%) for stage IV, 1 out of 11 (9%) for stages I-III+stage IVs, P=0.0018). Based on these results, the relationship between expression of ARID3b and neuroblastoma at stage IV was suggested.

TABLE 1

| Tissue | Sample Number | MYCN Positive | MYCN p value | ARID3b Positive | ARID3b p value | ARID3b-MYCN Positive | ARID3b-MYCN p value |
|---|---|---|---|---|---|---|---|
| Normal | 602 | 188 | 0.98 | 32 | 1 | 26 | 0.97 |
| Tumors | | | | | | | |
| Down syndrome, transient myeloproliferative disorder | 9 | 8 | 0.0013 | 0 | 1 | 0 | 1 |
| Adenocarcinoma | 11 | 1 | 0.99 | 3 | 0.07 | 0 | 1 |
| Adenocarcinoma barretts esophagus | 16 | 5 | 0.7 | 0 | 1 | 0 | 1 |
| Adenoma, pituutary | 4 | 1 | 0.81 | 1 | 0.32 | 0 | 1 |
| Alveolar rhabdomyosarcoma | 15 | 15 | 1.20e−07 | 0 | 1 | 0 | 1 |
| Astrocytoma | 100 | 70 | 2.56e−13 | 0 | 1 | 0 | 1 |
| Bladder cancer | 41 | 18 | 0.14 | 0 | 1 | 0 | 1 |
| Breast cancer | 606 | 123 | 1 | 0 | 1 | 0 | 1 |
| Colon cancer | 79 | 18 | 0.99 | 2 | 1 | 0 | 1 |
| Embryonic rhabdomyosarcoma | 15 | 15 | 1.20e−07 | 1 | 0.76 | 1 | 0.59 |
| Ganglioneuroma | 3 | 1 | 0.72 | 0 | 1 | 0 | 1 |
| Glioblastoma | 18 | 13 | 0.0013 | 0 | 1 | 0 | 1 |
| Acute lymphoblastic leukemia (ALL) | 204 | 31 | 1 | 34 | 0.00025 | 10 | 0.75 |
| Acute megakaryoblastic leukemia (AMgkL) | 8 | 5 | 0.1 | 2 | 0.16 | 1 | 0.38 |
| Leukemia other | 4 | 1 | 0.82 | 0 | 1 | 0 | 1 |
| T lymphoblastic leukemia | 87 | 48 | 5.78e−05 | 5 | 0.91 | 3 | 0.89 |
| Lung cancer | 49 | 14 | 0.86 | 1 | 0.99 | 1 | 0.95 |
| Lymphoma | 5 | 1 | 0.88 | 3 | 0.0065 | 0 | 1 |
| B cell lymphoma | 221 | 4 | 1 | 33 | 0.0022 | 1 | 1 |
| Neuroblastoma | 21 | 20 | 8.07e−09 | 11 | 4.48e−07 | 11 | 3.35e−09 |
| Oral squamous epithelium | 43 | 6 | 1 | 0 | 1 | 0 | 1 |
| Prostate cancer | 28 | 4 | 1 | 0 | 1 | 0 | 1 |
| Renal clear cell carcinoma | 22 | 1 | 1 | 0 | 1 | 0 | 1 |
| Small cell cancer cell lines | 10 | 1 | 0.99 | 3 | 0.055 | 0 | 1 |
| Squamous cell cancer | 8 | 0 | 1 | 1 | 0.53 | 0 | 1 |

In Table 1, the only tissue for which p values for both ARID3b and MYCN ("ARID3b-MYCN" in the table) were less than 0.0017 was neuroblastoma. Based on these results, it was suggested that it is possible to diagnose neuroblastoma more accurately by examining expression of both ARID3b and MYCN.

Example 6

Expression of ARID3b in neuroblastoma clinical samples was examined using microarray data available to the public. The present inventors used the data set of McArdle et al. (Carcinogenesis, 25:1599-1609 (2004)). This is because the data are available from ArrayExpress as described above in

INDUSTRIAL APPLICABILITY

The present invention provides a composition for treating neuroblastoma which contains an ARID3b inhibitor.

Sequence Listing Free Text

SEQ ID NO:1 Antisense oligonucleotide for ARID3b designated as ARID3b AS1; nucleotides 1, 3, 4, 6, 9, 11, 14, 16, 19 and 20 are 2'-O,4'-C-methylene bridged nucleic acids (BNAs)

SEQ ID NO:2 Antisense oligonucleotide for ARID3b designated as ARID3b AS3; nucleotides 2, 4, 5, 8, 10, 11, and 16 are 2'-O,4'-C-methylene bridged nucleic acids (BNAs)

SEQ ID NO:3 Antisense oligonucleotide for ARID3b designated as ARID3b AS5; nucleotides 1, 2, 3, 4, 5, 6, 7, 8, 11, 12, 13 and 20 are 2'-O,4'-C-methylene bridged nucleic acids (BNAs)

SEQ ID NO:4 Oligonucleotide designated as ARID3b AS5 scramble-1; nucleotides 1, 6, 8, 10, 12, 13, 16 and 18 are 2'-O,4'-C-methylene bridged nucleic acids (BNAs)

SEQ ID NO:5: Oligonucleotide designated as ARID3b AS5 scramble-2; nucleotides 1, 4, 6, 8, 10, 11, 14 and 16 are 2'-O,4'-C-methylene bridged nucleic acids (BNAs)

SEQ ID NO:6 Oligonucleotide designated as ARID3b RNAi(5) S; nucleotides 20 and 21 are deoxyribonucleotides SEQ ID NO:7 Oligonucleotide designated as ARID3b RNAi(5) A; nucleotides 20 and 21 are deoxyribonucleotides

The invention claimed is:

1. A method for treating neuroblastoma in a subject, which comprises administering an ARID3b inhibitor.

2. The method according to claim 1, wherein the ARID3b inhibitor is an antisense oligonucleotide or an siRNA for ARID3b mRNA.

3. A method for determining neuroblastoma in a subject, which comprises measuring the expression of ARID3b in a cell from the subject, compared to the amount in normal cells, with at least an antibody against ARID3b, or an oligonucleotide that is capable of annealing to an ARID3b-encoding gene or a sequence complementary thereto.

4. The method according to claim 3, wherein the oligonucleotide contains a sequence of consecutive 15 to 100 nucleotides selected from an ARID3b-encoding gene or a sequence complementary thereto.

* * * * *